(12) United States Patent
Busiashvili

(10) Patent No.: US 8,865,209 B1
(45) Date of Patent: Oct. 21, 2014

(54) COMBINED SUBLINGUAL AND GASTRO-INTESTINAL DELIVERY METHOD OF A LIQUID MEDICATION IN A SINGLE VOLUME LIMITED DOSE

(71) Applicant: Yuri Busiashvili, Pacific Palisades, CA (US)

(72) Inventor: Yuri Busiashvili, Pacific Palisades, CA (US)

( * ) Notice: Subject to any disclaimer, the term of this patent is extended or adjusted under 35 U.S.C. 154(b) by 0 days.

(21) Appl. No.: 14/291,927

(22) Filed: May 30, 2014

(51) Int. Cl.
*A61K 9/48* (2006.01)
*A61K 9/66* (2006.01)
*A61K 31/21* (2006.01)
*A61K 31/4418* (2006.01)

(52) U.S. Cl.
CPC ............ *A61K 9/4808* (2013.01); *A61K 31/4418* (2013.01)
USPC ............ 424/451; 424/455; 424/434; 514/509

(58) Field of Classification Search
USPC ............................ 424/451, 455, 434; 514/509
See application file for complete search history.

(56) References Cited

U.S. PATENT DOCUMENTS 7,279,457 B2    10/2007   Pohl et al.
8,361,497 B2    1/2013    Miller

*Primary Examiner* — Gina C Justice
(74) *Attorney, Agent, or Firm* — Ralph D. Chabot

(57) ABSTRACT

A method is disclosed for self-administered delivery of a pre-determined amount of liquid medication where a portion of the liquid medication is administered sublingually and the remaining portion is swallowed for and gastro-intestinal absorption.

11 Claims, 2 Drawing Sheets

COMBINED SUBLINGUAL AND GASTRO-INTESTINAL DELIVERY METHOD OF A LIQUID MEDICATION IN A SINGLE VOLUME LIMITED DOSE

BACKGROUND OF THE INVENTION

Oral delivery of medications is one of the most frequent techniques utilized for delivering medication to the body. One of the most popular delivery mechanisms is the capsule. The background of U.S. Pat. No. 8,361,497 issued to Miller provides a detailed description into the history and present techniques for capsule manufacture and is hereby incorporated by reference.

Capsules containing medication for oral intake is usually swallowed since it is designed for delivery of the medication to the stomach, where the capsule dissolves within 20 to 30 minutes and the medication is absorbed into the bloodstream.

In certain medical emergencies like acute coronary insufficiency, angina, hypertensive crisis, life threatening arrhythmias, epileptic aura seizures, it is required to deliver the medication to the bloodstream in one to two minutes. That could be accomplished by direct intravenous infusion of medication which is the preferred route used in medical emergencies in a hospital setting.

While intravenous injection is the fastest way to deliver a medication to the bloodstream, self-administration via intravenous injection is not a common practice.

The only other for delivery of medication within minutes to the bloodstream is sublingual administration or rectal instillation. Nitroglycerin is the only example that is used intravenously, sublingually as a liquid or tablet or rectally as an ointment. In all situations, the medication reaches the bloodstream almost immediately manifesting the effect by headache.

Liquid nitroglycerin given via pumpspray sublingually is competitive even when the intracoronary route of nitroglycerin administration is used in a catheterization laboratory. One problem with use of a pumpspray is that it is manufactured to delivery 60-200 doses. Such spray container has no limit on the number of doses a patient can administer in rapid succession. Thus, the possibility exists for the patient to overdose by spraying multiple doses with potential to incur life threatening side effects such as syncope, drop-attacks, etc.

SUMMARY OF THE INVENTION

Described herein is a capsular method of self-administration used in medical emergencies whereby a portion of the total volume of liquid medication contained in a capsule is applied to the sublingual area of a human. The medication remaining in the capsule can thereafter be swallowed for absorption in the gastro-intestinal tract. The therapeutic amount of liquid medication addressed by my invention has a volume of at least 0.2 ml and less than 1 ml and more preferably, less than 0.5 ml.

Accordingly, my invention describes a device and a method for delivery of a therapeutic liquid medication in a single volume limited dose partially delivered sublingually and partially delivered to the gastro-intestinal tract.

In a most preferred embodiment of my method, a therapeutic amount of medication is delivered to a human by providing a capsule having an outer wall that is dissolvable in the gastro-intestinal tract of a human and the capsule contains a pre-determined volume of medication where a portion of the pre-determined volume is discharged from the capsule into the mouth of an individual requiring the medication for sublingual absorption; and, thereafter, the capsule is ingested so that it will be dissolved and the portion of the medication remaining in the capsule will be absorbed in the gastro-intestinal tract.

The method described herein has the following benefits:

First, the ability to limit the overall volume of self-administered liquid medication to a maximal allowable dose for a single use to prevent an overdose, such as that which may occur by "double clicking", as is possible when using a multi-dose nitroglycerin pump spray container. Thus, the maximal allowable dose is synonymous with the term therapeutic amount.

Second, is the ability to deliver sublingually very small volumetric doses using a capsular delivery method.

Another benefit is the ability to deliver via the capsule a maximal allowable amount of a liquid medication for a single use; partially under the tongue and the remaining liquid medication in the capsule to the stomach and intestines. The combination of absorption sublingually followed by absorption within stomach and/or intestines allows rapid absorption as well as a more prolonged duration of absorption of the medication to the blood stream.

Finally, a sublingual capsular method of delivery is equivalent to intravenous delivery in its efficiency and rapid action when self-administration of a liquid medication is a matter of necessity without alternative in medical emergencies.

A preferred method for delivery of a therapeutic amount of medication to a human according to my invention comprises the steps of:

providing a capsule containing a therapeutic amount of medication;

discharging a portion of said therapeutic amount of medication from said capsule onto the sublingual area of a human; and, thereafter, ingesting said capsule containing the remaining portion of said therapeutic amount of medication.

Thus, the device of my invention is a modified capsule form which is capable of having discharged from it a portion of the therapeutic amount for sublingual application with the portion remaining in the capsule capable of being swallowed and absorbed in the user's stomach and/or intestines. The capsule can be easily carried and is less bulky than a spray canister. Furthermore, the capsule is a single-dose delivery system containing a pre-determined therapeutic amount of medication. Medication contemplated for use by my invention includes concentrated liquid medication forms such as Nifedipine and Nitroglycerin. The capsule may be provided in a sealed package which requires the capsule to be pushed through a thin film backing for additional protection. This type of package is commonly available.

The intended purpose of my invention is to deliver a portion of the therapeutic amount sublingually which will alleviate the patient's acute condition in as short a time as one minute and thereafter ingest the remaining portion of the therapeutic amount which will provide a more prolonged duration of the medication in the human's bloodstream.

It is to be understood that my invention will work only with those medications which are liquid in a concentrated form in which the therapeutic amount can be retained in a capsule. A container having liquid medication in excess of 1 ml discharged completely into the mouth would tend to be comingled with a human's saliva and swallowed defeating the purpose of my invention which is to deposit no more than a few drops (i.e. preferably no more than 0.5 ml) of medication underneath the tongue for sublingual absorption and then the portion remaining in the capsule swallowed to achieve a longer lasting effect. Since sublingual absorption results in medication entering the bloodstream almost instantaneously, sublingual absorption in combination with gastro-intestinal absorption which takes about 20-30 minutes should result in a longer lasting therapeutic effect. In other words, my method will not only deliver medication to the bloodstream almost immediately because of the rich venous blood flow in the sublingual area, but also that medication is entering the bloodstream approximately 20 minutes apart means that the duration of medicine in the bloodstream should be longer than if medication is only delivered sublingually or ingested.

Numerous embodiments can be designed for hole alignment suitable for discharge of a portion of the medication contained in a capsule.

In one embodiment of my device, the capsule comprises a base and cap. Preferably, this embodiment includes a pair of apertures, one aperture on the cap and the other on the base, where the capsule is in a first position in which the aperture pair are offset from each other. The base and cap are rotatable relative to each other and can be rotated to a second position where the apertures are aligned forming an opening for a portion of the medication located within the capsule to be discharged for sublingual delivery. With respect to the sidewall of the base and cap, one has an inside diameter slightly greater than the outside diameter of the other to fit in. The sidewalls overlap each other by a short length, approximately 1.5 mm-5 mm as is well known by those having skill in the art. This overlap of sidewalls is defined as an overlap area.

The cross-sectional area of the holes is collectively of sufficient size for discharge of the medication approximately 1 mm in diameter. The holes on both the cap and base are located in the overlap area.

Once the opening is formed, the capsule can be squeezed to discharge a portion of the therapeutic amount of medication. The discharge portion will most likely be no more than a few drops which will be a quantity sufficient to maintain in the sublingual area under the tongue. The capsule can thereafter be swallowed which will result in the remainder of the therapeutic amount left within the capsule to be absorbed in the stomach and/or intestines.

Rather than use of a capsule having separate cap and base portions, a single-piece or uniform cap structure could also be utilized. In a preferred structure, the capsule would have a sufficiently thin sidewall to be collapsible in response to an inward force applied by a thumb and forefinger grasping the capsule. The capsule would further incorporate a closed opening. The closed opening could involve any number of designs such as a nipple; or include a removable obstruction where an aperture is initially sealed using a removable plug or adhesive strip. Once any obstruction such as a plug or strip is removed, the forefinger and thumb of a single hand would grasp the capsule, position the closed opening above the sublingual area of a human's mouth and apply pressure to the capsule sidewall causing a portion of the therapeutic medication within the capsule to discharge onto the sublingual area. The capsule can thereafter be swallowed for gastro-intestinal absorption of the remaining medication. Another design would be to incorporate a thinner wall section located at the end of the capsule to act as a rupture disc which, in response to external force applied to the capsule body would fail and permit a portion of the liquid medication to be discharged.

For a nipple design outlet from the capsule, the nipple would be located at one end having an enlarged capsule wall thickness with through and through fissures as tributaries confluent towards the apex of the nipple, which can express a portion of the liquid content of the capsule when pressure is applied with the thumb and forefinger to the body of the capsule.

An alternative method for delivery of a therapeutic amount of medication to a human according to my invention consists of the following steps:

providing a capsule containing a therapeutic amount of medication;

discharging a portion of said therapeutic amount of medication from said capsule onto the sublingual area of a human; and, thereafter, ingesting said capsule containing the remaining portion of said therapeutic amount of medication.

DESCRIPTION OF THE PREFERRED EMBODIMENT

The figures provided herein are not drawn to scale and are provided for representational and instructional purposes.

Figure 1A:
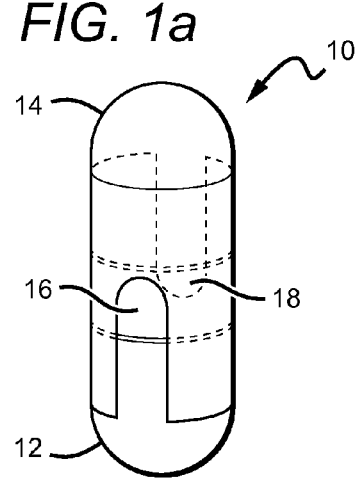
FIG. 1*a* is a perspective view of a capsule made according to my invention in a closed position.
Figure 2:
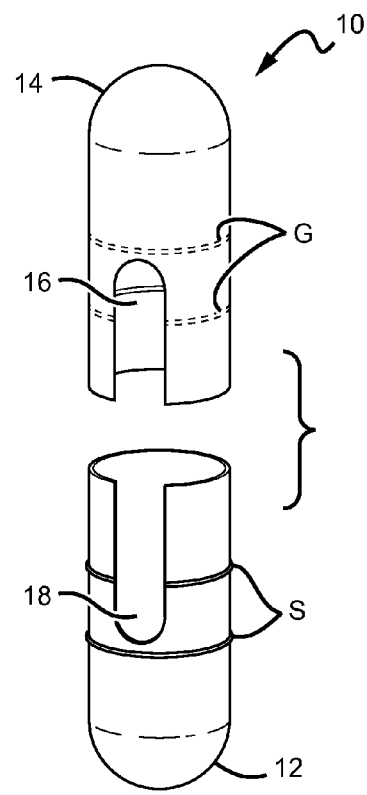
FIG. 2 is an exploded view of the capsule illustrated in FIGS. 1*a* and 1*b*.

FIG. 1*a* illustrates an enlarged view of a capsule 10 made according to my invention in a closed position. Referring to the exploded view of FIG. 2, capsule 10 consists of two halves, a base 12 and a cap 14, which overlap each other by approximately 2-4 mm. Base and cap can each be described as an open mid-segment cylinder each having a slightly different circumferential diameter from the other. A de minimis annular region exists when base 12 and cap 14 are fitted together as shown in FIG. 1*a* to prevent leakage of the liquid medication contained within capsule 10. Base 12 has orifice 18 extending from its open end and further includes a pair of spaced apart circumferential ridges S in parallel relation. Cap 14 has orifice 16 extending from its open end and further includes a pair of spaced apart circumferential grooves G in parallel relation. When base 12 and cap 14 are fitted together, as shown in FIG. 1*a*, a respective ridge S will be slidably fitted in a respective groove G to act as a seal. Orifices 16 and 18 are originally in a closed position, preferably contra lateral to one another. Capsule 10 is filled with a therapeutic amount of liquid medication (not shown).

Figure 1B:
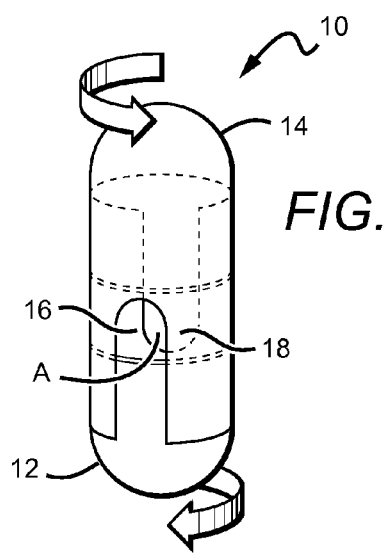
FIG. 1*b* is a perspective view of a capsule made according to my invention rotated toward an open position.

When a medical emergency occurs requiring the medication to be administered, capsule 10 is rotated from its first position illustrated in FIG. 1*a* to a second position in which orifaces 16 and 18 are aligned to form opening A. FIG. 1*b* illustrates the rotation of base 12 and cap 14 toward the second position.

Figure 3:
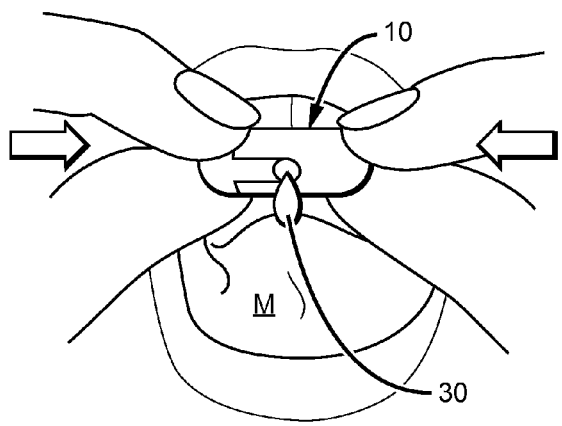
FIG. 3 is a perspective view of how the medication is delivered from the capsule to the sub-lingual area.

A portion of the therapeutic amount of medication 30 is discharged from capsule 10 by applying squeezing the capsule as represented in FIG. 3. Medication is deposited onto the sublingual area of the mouth M. The medication remaining within capsule 10 is swallowed for ingestion in the stomach and/or intestines.

Figure 4A:
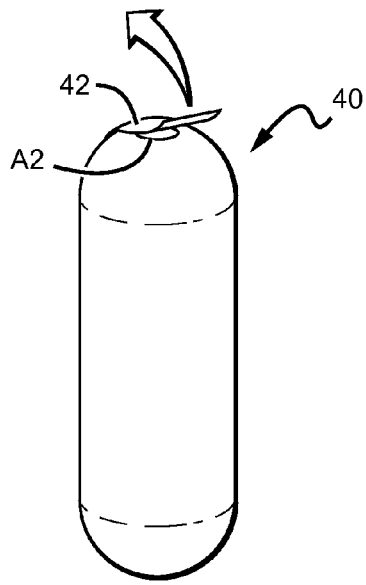
FIG. 4*a* is a first alternative embodiment with the aperture located on one end of the capsule.
Figure 4B:
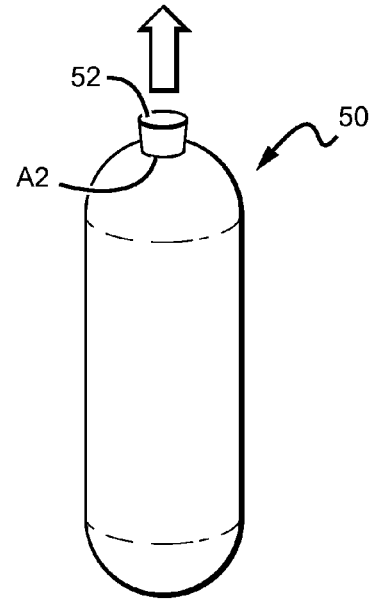
FIG. 4*b* is a second alternative embodiment with the aperture located on one end of the capsule.
Figure 4C:
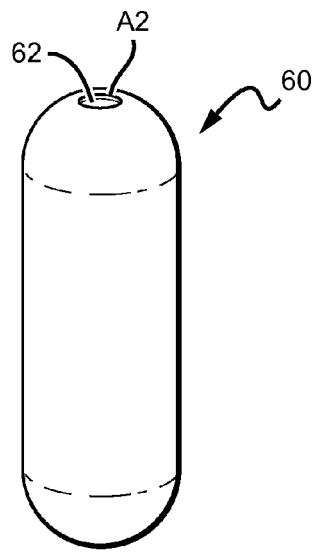
FIG. 4*c* is a third alternative embodiment with the aperture located on one end of the capsule.

Referring to FIGS. 4a, 4b and 4c, three alternative embodiments are presented which illustrate variations of a removable obstruction. FIG. 4a illustrates a capsule 40 having a removable adhesive strip 42 which covers aperture A2. FIG. 4b illustrates a capsule 50 having a removable plug 52 which covers aperture A2. FIG. 4c illustrates a capsule 60 having an inactivated aperture; essentially a reduced wall area 62 similar to a rupture disc which will rupture upon sufficient pressure applied to the capsule sidewall thus creating aperture A2.

Figure 5:
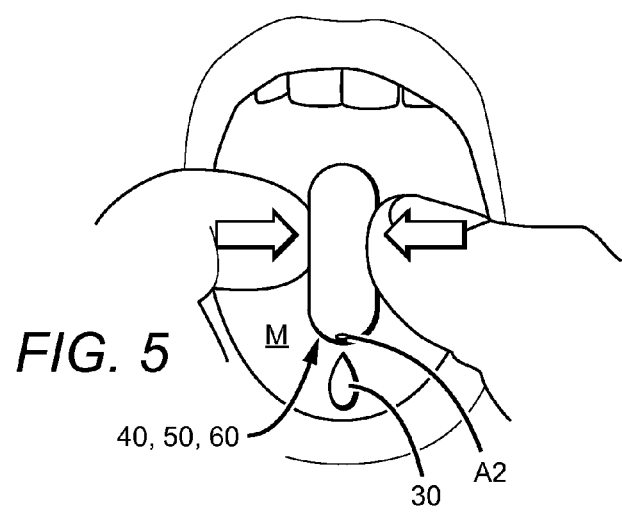
FIG. 5 is a perspective view of the capsule being grasped by the thumb and forefinger of one hand.

A portion of the therapeutic amount of medication 30 is discharged from capsule 40, 50, or 60 by applying force to the outer wall as shown in FIG. 5. Medication is deposited onto the sublingual area of the mouth M. The medication remaining within capsule 40, 50, or 60 is swallowed for ingestion in the stomach and/or intestines.

Group Study: Sublingual Use of Nifedipine for Urgent Therapy in Hypertensive Crisis.

Patients having a blood pressure measurement of at least 180 mm Hg were the subject of the study. All were treated with Nifedipine 10 mg in a liquid capsular form, the capsular content, measured to be 12 drops using a 12 gauge syringe and having a volume of 0.5 ml. The patients were randomly divided in 2 groups:

Group #1. Ingested Nifedipine 10 mg in capsular form.

Group #2. Nifedipine 10 mg in a capsule was given sublingually and ingested. A portion of the therapeutic amount was applied sublingually in the amount of 8 drops or two-thirds of capsule capacity. The capsule containing the residual medication was thereafter swallowed by the patient.

Patients were instructed to maintain the medication on the sublingual area and avoid comingling with saliva for as long as possible.

Blood pressure for each patient was measured in the same quiet room with the same blood pressure cuff. Each patient's arm was placed horizontally on an arm support chair extension. Blood pressure was repeatedly recorded every 5 minutes for one hour.

200 patients participated in the study; 100 in each group.

Results

In each group Nifedipine caused significant lowering of systolic blood pressure: maximal average drop of systolic blood pressure was 30 mm Hg.

For group 1 patients, the maximal effect on average was achieved at 30 minutes after oral intake of medication and was lasted for the duration of the test.

For group 2 patients, the maximal effect on average was achieved at 10 minutes after sublingual administration with the remainder being ingested. The reduced blood pressure effect lasted for the duration of the test.

There were no significant side effects reported by any of the patients in either group.

Diastolic blood pressure did not show any statistically significant fluctuations as a result of sublingual or ingested administration of Nifedipine.

CONCLUSIONS

1. Nifedipine in a 10 mg capsule liquid composition provides the same level of antihypertensive effect (i.e. reduced blood pressure), regardless whether completely ingested or when a portion of the 10 mg is taken sublingually followed by ingestion of the remainder of the medication.

2. The maximum anti-hypertensive effect was achieved in 10 minutes with the sublingual/ingestion combination of Group 2, vs. 30-40 minutes when taken orally by patients in Group 1.

3. Sublingual administration of a portion of the therapeutic amount resulted in beneficial effects noticeable at the first blood pressure reading 5 minutes after administration vs 25 minutes when the therapeutic amount is ingested.

4. The beneficial effects of sublingual administration of Nifedipine are not affected by earlier intake of other antihypertensive medications by the same patient within 24 hours. Patients with a history of calcium channel blocker intake within 24 hours were excluded from the study due to Nifedipine belonging to the group of calcium channel blocker antihypertensive medications.

5. No significant side effects were observed in either group studied.

I claim:

1. A method for delivery of a therapeutic amount of liquid medication in a medical emergency to a human comprising the steps of:
   providing a capsule containing a therapeutic amount of liquid medication;
   discharging a portion of said therapeutic amount of liquid medication from said capsule onto the sublingual area of a human; and,
   thereafter, ingesting said capsule containing the remaining portion of said therapeutic amount of liquid medication.

2. The method of claim 1 where said capsule further comprises an exterior wall and two ends and having an aperture located at one end for said discharge of a portion of said therapeutic amount of liquid medication, said capsule of a sufficient size to be gripped by a human using the thumb and forefinger of one hand; and where said discharging step comprises positioning said capsule in the human's mouth so that said aperture is facing the human's sublingual area and applying pressure to the exterior wall of said capsule for discharging said portion.

3. The method of claim 2 wherein said capsule further comprises a removable adhesive strip covering said aperture.

4. The method of claim 2 wherein said capsule further comprises a removable plug disposed within said aperture.

5. The method of claim 2 wherein said capsule further comprises a wall thickness at one of said ends which is thinner than at the other end and can be ruptured upon a sufficient force applied to the exterior wall of said capsule.

6. The method of claim 1 where said capsule further comprises at least two apertures for discharge of a portion of said therapeutic amount of medication; said capsule of a sufficient size to be gripped by the human using the thumb and forefinger of each hand, said capsule further comprising a base having an upward extending sidewall and a cap having a downward extending sidewall, where said cap and said base are rotatable relative to one another and where one of said sidewalls overlaps the other by between 2 mm-4 mm and which defines an overlap area, within said overlap area said cap and said base have a respective aperture set in a first position where said cap aperture is not aligned with said base aperture, said capsule rotatable to a second position where both apertures align to form an opening used as a discharge passage for a portion of said therapeutic amount of medication; and where said discharging step comprises rotating said cap relative to said base to displace from said first position to said second position, gripping said capsule with the forefinger and thumb of each hand; positioning said capsule in the human's mouth so that said aperture is facing the human's sublingual area, and applying pressure to the exterior wall of said capsule for discharging said portion of said therapeutic amount of medication upon a portion of the human's sublingual area.

7. The method of claim 6 wherein said capsule further comprises a ridge and groove combination to control the rotational movement from said first position to said second position.

8. The method of claim 1 where said liquid medication is selected from the group consisting of Nifedipine and Nitroglycerin.

9. The method of claim 2 where said liquid medication is selected from the group consisting of Nifedipine and Nitroglycerin.

10. The method of claim 6 where said liquid medication is selected from the group consisting of Nifedipine and Nitroglycerin.

11. A method for delivery of a therapeutic amount of liquid medication to a human comprising the steps of:
   providing a capsule having an outer wall that is dissolvable in the gastro-intestinal tract of a human; said capsule containing a therapeutic volume of liquid medication;
   discharging a portion of said therapeutic amount of liquid medication from said capsule for sublingual absorption; and,
   thereafter, ingesting said capsule for gastro-intestinal absorption of the remaining portion of said therapeutic amount of medication.

\* \* \* \* \*